US012697335B2

(12) United States Patent (10) Patent No.: US 12,697,335 B2
Allenbach et al. (45) Date of Patent: Aug. 4, 2026

(54) METHOD FOR TREATING IMMUNE TOXICITIES INDUCED BY IMMUNE CHECKPOINT INHIBITORS

(71) Applicants: ASSISTANCE PUBLIQUE—HÔPITAUX DE PARIS, Paris (FR); SORBONNE UNIVERSITÉ, Paris (FR); INSTITUT NATIONAL DE LA SANTÉ ET DE LA RECHERCHE MÉDICALE (INSERM), Paris (FR)

(72) Inventors: Yves Allenbach, Paris (FR); Joe-Elie Salem, Paris (FR); Céline Anquetil, Paris (FR)

(73) Assignees: ASSISTANCE PUBLIQUE-HÔPITAUX DE PARIS, Paris (FR); SORBONNE UNIVERSITÉ, Paris (FR); INSTITUT NATIONAL DE LA SANTÉ ET DE LA RECHERCHE MÉDICALE (INSERM), Paris (FR)

( * ) Notice: Subject to any disclaimer, the term of this patent is extended or adjusted under 35 U.S.C. 154(b) by 751 days.

(21) Appl. No.: 18/018,658

(22) PCT Filed: Jul. 29, 2021

(86) PCT No.: PCT/EP2021/071319
§ 371 (c)(1),
(2) Date: Jan. 30, 2023

(87) PCT Pub. No.: WO2022/023490
PCT Pub. Date: Feb. 3, 2022

(65) Prior Publication Data
US 2023/0293531 A1 Sep. 21, 2023

(30) Foreign Application Priority Data
Jul. 30, 2020 (EP) ..................................... 20305873

(51) Int. Cl.
*A61K 31/519* (2006.01)
*A61P 9/00* (2006.01)
*C07K 16/28* (2006.01)
(52) U.S. Cl.
CPC .............. *A61K 31/519* (2013.01); *A61P 9/00* (2018.01); *C07K 16/2818* (2013.01); *C07K 16/2827* (2013.01); *C07K 16/2896* (2013.01)
(58) Field of Classification Search
CPC ................................ A61K 31/519; A61P 9/00
See application file for complete search history.

(56) References Cited

U.S. PATENT DOCUMENTS

2014/0357557 A1 12/2014 Cole et al.
2018/0258088 A1 9/2018 Fatheree et al.

FOREIGN PATENT DOCUMENTS

WO WO-2014078486 A1 * 5/2014 .............. A61P 35/02
WO 2020092792 A2 5/2020
WO 2020161045 A1 8/2020
WO 2021174024 A1 9/2021

OTHER PUBLICATIONS

Ansel, H.C. et al. Pharmaceutical Dosage Forms and Drug Delivery Systems, Lippincott Williams & Wilkins, 7th ed., 1999, pp. 48-53 (Year: 1999).*
Inayat, F. et al. BMJ Case Rep., 2018, 1-4 (Year: 2018).*
Nguyen, L.S. et al., Journal for Immunotherapy of Cancer, 2022, 10, 1-5 (Year: 2022).*
Yang, Y., Ohio State University Comprehensive Cancer Center, NCT06470971, Jan. 20, 2026, https://clinicaltrials.gov/study/NCT06470971?tab=study (Year: 2026).*
Yeleswaram, S. et al., Clinical Immunology, 2020, 218, 1-6 (Year: 2020).*
Kang, J.H. et al., Trends in Immunology, 2021, 42(4), 293-311 (Year: 2021).*
Joe-Elie Salem et al.: "Abatacept/Ruxolitinib and Screening for Concomitant Respiratory Muscle Failure to Mitigate Fatality of Immune-Checkpoint Inhibitor Myocarditis," Research Article, Cancer Discovery, 2023, pp. OF1-OF38.
Jiun-Ruey Hu et al.: "Cardiovascular toxicities associated with immune checkpoint inhibitors," Cardiovascular Research (2019) 115, 854-868.
Johnson Clinical Trial: "Itacitinib for the Treatment Steroid Refractory Immune Related Adverse Events Arising From Immune Checkpoint Inhibitors," Clinical Trials, National Library of Medicine, 2024, pp. 1-14.
Qing Liu et al.: "Tofacitinib for the treatment of immune-related adverse events in cancer immunotherapy: a multi-center observational study," Journal of Translational Medicine, vol. 22, No. 803, 2024, pp. 1-11.
Michael A. Postow et al.: "Immune-Related Adverse Events Associated with Immune Checkpoint Blockade," The England Journal of Medicine, vol. 378, No. 2, 2018, pp. 158-168.
Sana Haider et al.: "Novel treatments for novel side effects: a case report and review of baricitinib use in the treatment of chronic inflammatory demyelinating polyneuropathy caused by immune checkpoint inhibitor use," Journal for ImmunoTherapy of Cancer, vol. 11, 2023, pp. 1-4.
International Search Report and Written Opinion issued on Nov. 5, 2021 for corresponding PCT Application No. PCT/EP2021/071319.
Esfahani, Khashayar et al., "Moving towards personalized treatments of immune-related adverse events", Nature Reviews Clinical Oncology, vol. 17, No. 8, 2020, pp. 504-515 XP037198614.
Mcgrath, Emer R. et al., "Autoimmune Myopathies: Updates on Evaluation and Treatment", Neurotherapeutic Elsevier Inc, vol. 15, No. 4, 2018, pp. 976-994 XP036908222.

(Continued)

*Primary Examiner* — John S Kenyon
*Assistant Examiner* — Sara Elizabeth Bell
(74) *Attorney, Agent, or Firm* — POLSINELLI PC

(57) ABSTRACT

The invention relates to the use of a JAK inhibitor for treating or preventing adverse events in patient treated with an immune checkpoint inhibitor, or for treating cancer in combination with an immune checkpoint inhibitor.

21 Claims, 1 Drawing Sheet

(56) References Cited

OTHER PUBLICATIONS

Semper, H. et al., "Drug-induced myocarditis after nivolumab treatment in a patient with PDL1-negative squamous cell carcinoma of the lung", Lung Cancer, vol. 99, 2016, pp. 117-119 XP002791618.

Xiaoxiang Zhou et al., "Are immune-related adverse events associated with the efficacy of immune checkpoint inhibitors in patients with cancer? A systematic review and meta-analysis", BMC Medicine, vol. 18, No. 1, 2020 XP055760000.

Salem, Joe-Elie, "Abatacept for Severe Immune Checkpoint Inhibitor-Associated Myocarditis", 2019, pp. 2377-2379 XP055854888.

Ravneet Bajwa et al., "Adverse Effects of Immune Checkpoint Inhibitors (Programmed Death-1 Inhibitors and Cytotoxic T-Lymphocyte-Associated Protein-4 Inhibitors): Results of a Retrospective Study," J. Clin Med Res., vol. 11, No. 4, 2019, pp. 225-236.

Jennifer Cautela et al., "Intensified immunosuppresive therapy in patients with immune checkpoint inhibitor-induced myocarditis," Journal for Immuno Therapy of Cancer, vol. 8, 2020, pp. e001887.

Sabrina Ceeraz et al., "Immune checkpoint receptors in regulating immune reactivity in rheumatic disease," Arthritis Research & Therapy, vol. 16, 2014, pp. 1-12.

Chia-Yu Chen et al., "Treatment of pembrolizumab-induced cutaneous lesions with ruxolitinib," Science Direct, European Journal of Cancer, vol. 113, 2019, pp. 69-71.

Brian W. Dymock et al., "Inhibitors of JAK2 and JAK3: an update on the patent literature 2010-2012," Expert Opinion, pp. 1-53.

Esfahani, Khashayar et al., "Tofacitinib for Refractory Immune-Related Colitis from PD-1 Therapy", NThe New England Journal of Medicine, vol. 382, No. 24, 2020, pp. 2374-2375.

Anonymous, "Fludarabine," 2021, pp. 1-6.

Sarju Ganatra et al., "Immune Checkpoint inhibitor-Associated Myocarditis," The Oncologist, vol. 23, 2018, pp. 879-886.

Xingrui He et al., "Selective Tyk2 inhibitors as potential therapeutic agents: a patent review (2015-2018)," Expert Opinion on Therapeutic Patents, 2019, pp. 1-20.

K. Hilliard et al., "Alternaria Alternata Induces Pulmonary Inflammation in In Vivo and In Vitro Models of Asthma: Relative Contribution of Th2Cytokines," Online Abstract Issue.

Changhua Ji et al., "Myocarditis in Cynomolgus Monkeys Following Treatment with Immune Checkpoint Inhibitors," Translational Cancer Mechanism and Therapy, Clinical Cancer Research, 2013, pp. 4735-4748.

Douglas B. Johnson et al., "Fulminant Myocarditis with Combination Immune Checkpoint Blockade," New England Journal of Medecine, vol. 375, No. 18, 2016, pp. 1749-1755.

Jason G. Kettle et al., "Inhibitors of JAK-family kinases: an update on the patent literature 2013-2015, part 1," Expert Opinion on Therapeutic Patents, vol. 27, No. 2, 2017, pp. 127-143.

Jason G. Kettle et al., "Inhibitors of JAK-family kinases: an update on the patent literature 2013-2015, part 2," Expert Opinion on Therapeutic Patents, vol. 27, No. 2, 2017, pp. 145-161.

Robert Kiss et al., "Recent developments on JAK2 inhibitors: a patent review," Expert Opinion, 2010, pp. 471-495.

Robb D. Kociol et al., "Recognition and Initial Management of Fulminant Myocarditis," Circulation, 2020, vol. 141, pp. e1-e24.

Bharat Kumar et al., "Adverse Events Associated with Immune Checkpoint Blockade," New England Journal of Medicine, vol. 378, No. 12, 2018, pp. 1163-1165.

Christel J. Menet, "Toward selective TYK2 inhibitors as therapeutic agents for the treatment of inflammatory disease," Pharmaceutical Patent Analyst, vol. 3, No. 4, 2014, pp. 449-466.

Javid J. Moslehi et al., "Increased reporting of fatal immune checkpoint inhibitor-associated myocarditis," Correspondence, vol. 391, 2018, pp. 933.

Peter Norman, "Selective JAK1 inhibitor and selective Tyk2 inhibitor patents," Expert Opinion, vol. 22, No. 10, 2012, pp. 1233-1249.

Peter Norman, "Evaluation of WO2013125543, WO2013146963 and EP2634185: the first Tyk2 inhibitors from Tkeda and Sareum," Expert Opinion, vol. 24, No. 3, 2014, pp. 361-368.

Joe-Elie Salem, "The Lancet Oncology—Supplemental appendix," pp. 1-6.

Joe-Elie Salem et al., "Cardiovascular toxicities associated with immune checkpoint inhibitors: an observational, retrospective, pharmacovigilance study," Articles, The Lancet Oncology, vol. 19, 2018, pp. 1579-1589.

Aniruddh Som et al., "Immune checkpoint inhibitor-induced colitis: A comprehensive review," World Journal of Clinical Cases, vol. 7, No. 4, 2019, pp. 405-418.

Kazuko Tajiri et al., "Immune checkpoint inhibitor-related myocarditis," Japanese Journal of Clinical Oncology, vol. 48, No. 1, 2018, pp. 7-12.

Michiel Van Der Vlist et al., "Immune checkpoints and rheumatic diseases: what can cancer immunotherapy teach us?" Nature Reviews, 2016, pp. 1-12.

Giacomo Veronese et al., "Fulminant myocarditis: Characteristics, treatment, and outcomes," Anatol. J. Cardiol., vol. 19, 2018, pp. 279-286.

Daniel Y. Wang et al., "Fatal Txic Effects Associated With Immune Checkpoint Inhibitors—A Systematic Review and Meta-analysis," JAMA Oncology, 2018, pp. E1-E8.

Spencer C. Wei et al., "A Genetic Mouse Model Recapitulates Immune Checkpoint Inhibitor-Associated Myocarditis and Supports a Mechanism-Based Therapeutic Intervention," Research Brief, Cancer Discovery, 2021, pp. 614-625.

Lawrence J. Wilson, "Recent patents in the discovery of small molecule inhibitors of JAK3," Expert Opinion, vol. 20, No. 5, 2010, pp. 609-623.

Yu-Wen Zhou et al., "Immune Checkpoint Inhibitor-Associated Cardiotoxicity: Current Understanding on Its Mechanism, Diagnosis and Management," Frontiers in Pharmacology, vol. 10, Article 1350, 2019, pp. 1-20.

* cited by examiner

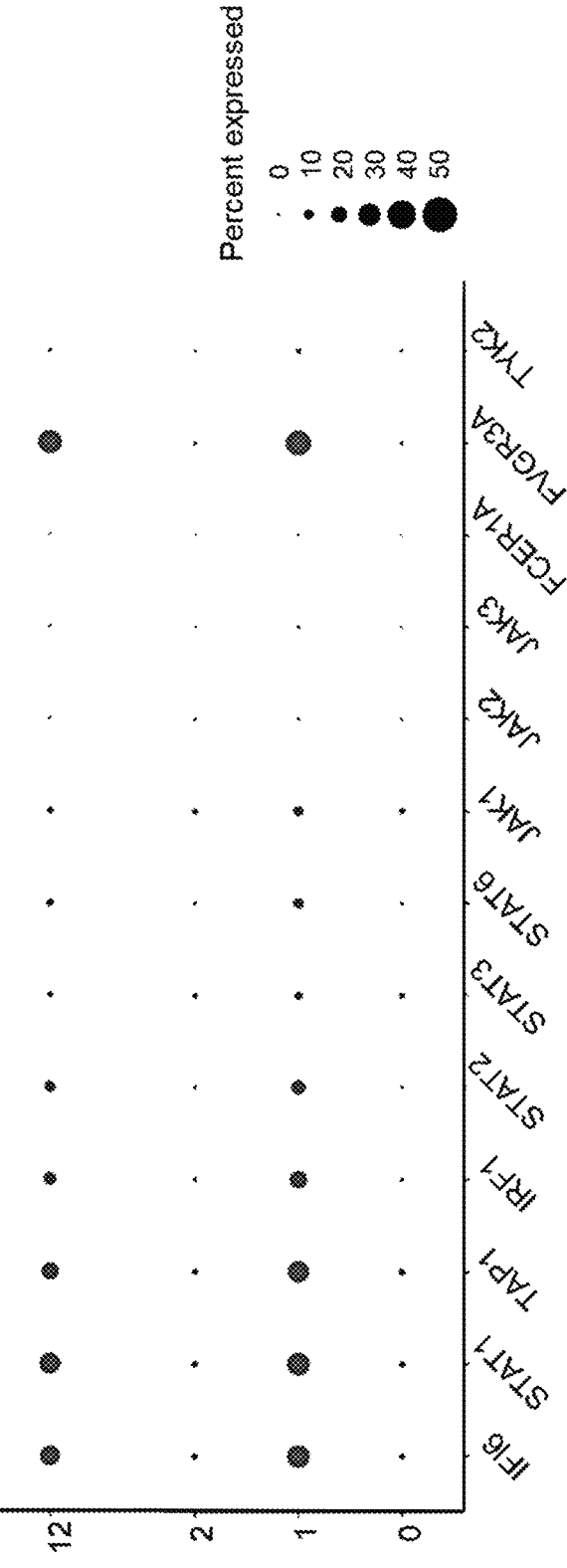

1

METHOD FOR TREATING IMMUNE TOXICITIES INDUCED BY IMMUNE CHECKPOINT INHIBITORS

CROSS-REFERENCE TO RELATED APPLICATIONS

This application is a national stage application (under 35 U.S.C. § 371) of PCT/EP2021/071319, filed Jul. 29, 2021, which claims benefit of European Application No. 20305873.0, filed Jul. 30, 2020, which are incorporated herein by reference in their entireties.

Checkpoint inhibitor therapy is a form of cancer immunotherapy that has revolutionized oncology treatment. It consists in targeting immune checkpoints, which are key regulators of the immune system that stimulate or inhibit its actions. Checkpoint therapy in oncology aims at blocking inhibitory checkpoints, which tumors use to protect themselves from attacks by the immune system, hence restoring immune system function and fighting the tumor.

The currently approved immune checkpoint inhibitors (ICI) target the molecules CTLA4 (Cytotoxic T-Lymphocyte associated protein 4), PD-1 (the transmembrane programmed cell death 1 protein, also called PDCD1 and CD279), and PD-L1, which is the PD-1 ligand (or CD274). PD-1 acts as a key regulatory role on T cell activities, and cancer-mediated upregulation of PD-L1 on the cancer cell surface may inhibit T cells recognition and action against these cells. Antibodies against PD-1 or PD-L1 block the interaction between these proteins and allow T-cells to attack the tumor.

Another inhibitory checkpoint targeted in oncology is CTLA-4 (CD152), a protein receptor constitutively expressed in regulatory T cells and upregulated in conventional T cells after activation. It acts as an inhibitory switch of the immune system when it binds to CD80 or CD86 expressed on the surface of antigen-presenting cells.

However, the activation of the immune system after use of such immune checkpoint inhibitors may also lead to immune related adverse events (irAE) affecting potentially any organ.

Although rare, fulminant, and fatal irAE on ICI may occur in −0.36-1.23% of treated patients (Wang et al. JAMA Oncol 2018; 4:1721-8). Severe and fatal toxicities are more common with anti-CTLA4 therapies, particularly when combined with PD1 or PDL1 blockers. ICI induced myocarditis occurs rarely (<1%) but is the irAE with the highest fatality rate. In the largest case-series of 122 myocarditis cases worldwide, the fatality rate was reported to be 50% with an earlier onset and higher fatality rate with ICI combination therapy versus monotherapy (Salem et al. Lancet Oncol 2018; 19:1579-89). Interestingly, ICI myocarditis occurred generally after few ICI doses (n=1-3) and were often associated with concurrent muscular, pulmonary and hepatic irAE, including myositis (25%) with a peculiar phenotype often associated with oculomotor and diaphragmatic dysfunction. A main contributing cause of death in ICI myocarditis is early progressive and refractory cardiac electrical instability (heart blocks and ventricular arrhythmias) and cardiac dysfunction leading to cardiogenic shock, often resistant to intense immunosuppression.

While rigorous studies for the treatment of irAEs have not been performed, consensus guidelines recommend initial treatment with high-dose corticosteroids with progressive tapering and holding ICI (Brahmer et al, J Clin Oncol 2018; 36:1714-68). Corticosteroids doses range from bolus of 0.5-2 mg/kg/day of prednisone up to 1 g/day methylprednisolone, depending on severity of clinical presentation. If symptoms and laboratory findings do not improve or worsen with steroids, other immunosuppressive drugs (mycophenolate-mofetil, cyclophosphamide, cyclosporine, tacrolimus, mTors inhibitors, methotrexate, azathioprine, antithymocyte globulin, alemtuzumab, infliximab, and rituximab) can be considered, depending on organs affected. In case of associated myositis and/or myasthenia gravis, intravenous immunoglobulin or plasmapheresis can be considered when presentations are severe and/or corticosteroid-resistant. In a subset of patients with fulminant, and chronic toxicities, however, available immunosuppressants produce suboptimal results (i.e. the 1.23% of patients who die from PD1/CTLA4 blockade induced toxicities).

US20180258088 discloses new JAK inhibitors and provides a list of potential indications for use. The rational of US20180258088 is explained in particular in [0003]-[0006], which make clear that the essential goal for developing JAK inhibitors is to provide a treatment to asthma or various specific lung diseases.

provides putative other uses for JAK inhibitors. US20180258088 describes, in the examples, the testing of the compounds in vitro in Biochemical JAK Kinase Assays (assay 1), the in vitro testing for Cellular JAM Potency Assay (assay 2), the Pharmacokinetics in Plasma and Lung in Mouse (assay 3), a Murine (Mouse) Model of IL-13 Induced pSTAT6 Induction in Lung Tissue (assay 4): it shows in vitro inhibitory activity in this model which specifically is designed to involve the JAK pathway; no data as to a clinical difference between control and treated groups are provided), a Murine Model of *Alternaria alternata*-Induced Eosinophilic Inflammation of the Lung (assay 5): it is presented as a model for human asthma. It shows inhibition of alternaria-induced BALF eosinophils. It is to be noted that, as disclosed in Hilliard et al (Am J Respir Crit Care Med 193; 2016:A1471), it was known that *A. alternata* inflammation is induced, at least in part, by activation of the JAK-STAT3 pathway. The observed data was thus expected.

An in vitro IL-5 Mediated Eosinophil Survival Assay (assay 6): as indicated on [0332], it is known that IL-5 signals through JAK.

An in vitro Cellular JAK Potency Assay: Inhibition of IL-2/anti-CD3 Stimulated IFN.gamma. in Human PBMCs (assay 7): as indicated on [0336], it is known that IL-2 signals through JAK.

An in vitro Cellular JAK Potency Assay: Inhibition of IL-2 Stimulated pSTAT5 in CD4+ T Cells (assay 8), which also knowingly involves JAK-pathway through IL-2.

An in vitro Cellular JAK Potency Assay: Inhibition of IL-4 Stimulated pSTAT6 in CD3+ T Cells (assay 9): as indicated on [0345], it is known that IL-4 signals through JAK An in vitro Cellular JAK Potency Assay: Inhibition of IL-6 Stimulated pSTAT3 in CD3+ T Cells (assay 10): as indicated in [0004], IL-6 is known to be a cytokine implicated in asthma inflammation which signals through the JAK-STAT pathway.

In summary, the actual teachings of US20180258088 focus on the ability of the new compounds to inhibit the JAK pathway and their potential efficacy. The actual teachings don't demonstrate or even make it plausible that these compounds can be used for any kind of disease, such as the ones listed in the application.

WO 2020/092792 proposes to use a JAK1/2 inhibitor for treating and/or inhibiting cancer. The role of the inhibitor is to decrease expression of (or inhibits increased expression of) the checkpoint proteins PD-1, PD-L1, PD-L2, or B7 H3, and/or enhance T-cell killing of tumor cells, and/or enhance the anti-tumor effects of checkpoint inhibitors. This document doesn't suggest to use JAK inhibitors to reduce irAEs.

Esfahani et al, (2020, Nat Rev Clin Oncol. 2020 August; 17(8):504-515)) is a review discussing adverse effects of immune checkpoint inhibitors and how to treat them. This document mentions the JAK-STAT pathway as a potential way for treating these adverse effects (among multiple other ways). This document doesn't provide any data showing that JAK-inhibitors can be efficient and in fact emphasizes that their use for the treatment of irAEs in response to ICIs has yet to be reported. There is no reasonable expectation of success in this document, which at best would suggest conducting research programs.

US 2014/357557 pertains to the treatment of inflammatory or autoimmune diseases by JAK inhibitors, and doesn't describe nor suggest a use for treating ICIs-induced irAEs. It is not surprising that this document doesn't discuss irAEs, as the widespread use of ICI only started around 2016, and most of irAEs had thus not been identified at the time this document was published.

McGrath et al (Neurotherapeutics. 2018 October; 15(4): 976-994) discloses use of JAK-inhibitors for treating auto-immune diseases, but doesn't describe nor suggest a use for treating ICIs-induced irAEs.

Semper et al (Lung Cancer. 2016 September; 99:117-9) present a case of symptomatic drug induced myocarditis after nine cycles of nivolumab in a patient with efficient anticancer response, but doesn't describe nor suggest a use of JAK inhibitors for treating this adverse effect.

Zhou et al. (2020, BMC Medicine 18:87) is a review pertaining to a potential association between the occurrence of immune-related adverse events (irAEs) and clinical efficacy in patients undergoing treatment with immune checkpoint inhibitors (ICIs).

It is to be noted that the examples of the application show that irAE are a unique condition that is different from their spontaneous auto-immune counterparts and have different mechanisms of action.

The invention thus relates to a JAK inhibitor for use thereof for the treatment of immune-related adverse events induced by a treatment with an immune checkpoint inhibitor.

In particular, said immune-related adverse events induced by a treatment with an immune checkpoint inhibitor is not toxidermia (cutaneous lesions, such as skin rashes and/or ulcerations), colitis or arthritis.

The JAK inhibitor can also be used to prevent occurrence or recurrence of an immune-related adverse event induced by a treatment with an immune checkpoint inhibitor. In this embodiment, the JAK inhibitor is used in combination with the immune checkpoint inhibitor. In this embodiment, the patient receiving the ICI doesn't have any adverse event when the JAK inhibitor is administered. In other words, the administration of the JAK inhibitor is performed in the absence of any adverse event. The purpose is to avoid occurrence of such adverse events.

Such use is particularly adapted when the adverse event is a de novo event, i.e. is not related to a preexisting immune condition. In this embodiment, it is preferred when the patient has not been diagnosed with an auto-immune disease prior to the inset of the treatment with the immune checkpoint inhibitor.

The proposed use is also of particular interest when the adverse event is T-cell and/or macrophage driven, i.e. involving infiltration of CD4+ and/or CD8+ T cells and/or CD68+ macrophages, with minimal or no implication of antibodies (no presence of antibody deposits).

By JAK inhibitor, it is intended to designate a molecule that inhibits the activity of one or more of the Janus kinase family of enzymes, thereby interfering with the JAK-STAT signaling pathway. Some examples of effect of the JAK/STAT signaling pathway are production of colony-stimulating factor, prolactin, growth hormone, and many cytokines. Janus kinases (or JAKs) is an intracellular, non-receptor tyrosine kinase family consisting of four different subtypes, namely JAK1, JAK2, JAK3, and TYK2. JAK1, JAK2, and TYK2 are ubiquitously expressed, while JAK3 is mainly localized in hematopoietic cells.

JAK inhibitors have been proposed to be used for treating various diseases such as autoimmune diseases (in particular psoriasis, rheumatoid arthritis, inflammatory bowel disease, Sjogren's syndrome, Behcet's disease, multiple sclerosis, or systemic lupus erythematosus), immunological diseases or inflammatory diseases, central nervous system disorders, organ transplants, hyperproliferative diseases including cancer and myeloproliferative diseases, viral diseases, metabolic diseases and vascular diseases, pulmonary arterial hypertension, asthma, or chronic obstructive pulmonary disease. Tofacitinib has also been used in therapy for ulcerative colitis. All these use are linked to diseases that are not drug induced, and could be qualified as spontaneous.

Many inhibitors have been developed over the past 20 years, some of which being ubiquitous (inhibiting the activity of more than one kinases of the JAK family), and other being more specific (targeting essentially the kinase activity of only one member of the JAK family).

In an embodiment, the JAK inhibitor is a TYK2 inhibitor.

Inhibitors of TYK2 are described in the art, in particular in various patents such as the ones mentioned in Norman (Expert Opin. Ther. Patents (2014) 24(3):361-368), Norman (Expert Opin. Ther. Patents (2012) 22(10):1233-1249), Menet (Pharm. Pat. Anal. (2014) 3(4), 449-466) or He et al. (Expert Opin Ther Pat. 2019 February; 29(2):137-149).

In further details, DE102009015070A1 discloses N-[3-(4-aminopyrimidin-2-yl)aminophenyl] urea derivatives. WO2011113802 describes derivatives of 3H-imidazo[4,5-c] pyridin-4-amines and 7H-purin-6-amines, WO2012035039 describes derivatives of thiazolo[5,4-c]pyridin-4-amines and thiazolo[4,5-d]pyrimidin-7-amines and WO2012066061 describes derivatives of 2H-pyrazolo[4,3-c]pyri-din-2-amines and 2H-pyrazolo[3,4-d]pyrimidin-4-amines. WO2012000970 describes derivatives of aryl-substituted bicyclic amines, 5-phenyl-[1,2,4]triazolo[1,5-a]pyri-din-2-amine (triazolopyridine Tyk2 inhibitors), WO2012062704 describes derivatives of 2-aminopyrimi-dine, 2-amino-1,3,5-triazine and 2-aminopyridine (Monocyclic Tyk2 inhibitors), WO2013174895 describes pyrimidine based analogs as Tyk2 inhibitors, WO2015032423 describes substituted 5-amino-2-phenyloxazole-4-carboxamide which show a high selectivity for Tyk2 over Jak1, Jak2, and Jak3.

WO2015016206, WO2013146963 and WO2013125543 describe 2,4-diaminopyridine compounds (WO2013125543 relates to derivatives based on 1,5-dihydro-4H-pyrazolo[4,3-c]pyridine-4-one scaffold and WO2013146963 pertains to derivatives of 1-(2-arylaminopyrimidin-4-yl)-pyrrolidin-2-one), JP 2016-65023 describes 3-amino-1,5-dihydro-4H- pyrazolo[4,3-c]pyridin-4-one analogs. US20150299139, WO2015069310. U.S. Pat. No. 9,505,748, and WO20180162889 disclose compounds based on an imidazo [1,2-b]pyridazine scaffold. One can also mention WO2015089143, WO2017087590, WO2018067432 and WO2018093968. In particular, the compounds of WO2015016206 show a high Tyk2 inhibitory effect.

EP2634185 pertains to derivatives of 5-anilino-2-(2-halo-phenyl)-oxazole-4-carboxamide with nanomolar activity against Tyk2 and high selectivity over JAK1, JAK2 and JAK3.

In an embodiment, the JAK inhibitor is a JAK3 inhibitor.

JAK3 inhibitors are described in the art, in particular in patents and applications mentioned in Dymock and See (Expert Opin Ther Pat. 2013 April; 23(4):449-501) or Wilson (Expert Opin. Ther. Patents (2010) 20(5):609-623).

Of particular interest is Tofacitinib (3-[(3R,4R)-4-Methyl-3-[methyl(7H-pyrrolo[2,3-d]pyrimidin-4-yl)amino]piperi-din-1-yl]-3-oxopropanenitrile) that is currently used to treat rheumatoid arthritis, psoriatic arthritis, ankylosing spondy-litis and ulcerative colitis. It is disclosed in WO200142246 or U.S. Pat. No. 6,956,041.

One can also cite Decernotinib ((2R)-2-Methyl-2-[[2-(1H-pyrrolo[2,3-b]pyridin-3-yl)pyrimidin-4-yl]amino]-N-(2,2,2-trifluoroethy)butanamide) and PF-06651600 which are in clinical trials.

One can also cite Peficitinib (4-[[(1R,3S)-5-hydroxy-2-adamantyl]amino]-1H-pyrrolo[2,3-b]pyridine-5-carboxam-ide).

In an embodiment, the JAK inhibitor is a JAK2 inhibitor.

Inhibitors of JAK2 are known in the art, in particular in patents and applications mentioned in Dymock and See (Expert Opin Ther Pat. 2013 April; 23(4):449-501) or Kiss et al (Expert Opin Ther Pat. 2010 April; 20(4):471-95).

One can cite in particular Fedratinib (N-tert-Butyl-3-{5-methyl-2-[4-(2-pyrrolidin-1-yl-ethoxy)-phenylamino]-py-rimidin-4-ylamino}-benzenesulfonamide), disclosed in WO2007053452.

One can also cite Gandotinib (3-(4-Chloro-2-fluoroben-zyl)-2-methyl-N-(5-methyl-1H-pyrazol-3-yl)-8-(morpholi-nomethyl)imidazo[1,2-b]pyridazin-6-amine).

Of interest is also Lestaurtinib ((5S,6S,8R)-6-Hydroxy-6-(hydroxymethyl)-5-methyl-7,8,14,15-tetrahydro-5H-16-oxa-4b,8a,14-triaza-5,8-methanodibenzo[b,h] cycloocta[jkl] cyclopenta[e]-as-indacen-13(6H)-one), or Pacritinib ((16E)-11-[2-(1-Pyrrolidinyl)ethoxy]-14,19-dioxa-5,7,26-triazatetracyclo[19.3.1.1$^{2,6}$,1$^{8,12}$]heptacosa-1(25),2(26),3,5,8,10,12(27),16,21,23-decaene).

In an embodiment, the JAK inhibitor is a JAK1 inhibitor.

Inhibitors of JAK1 inhibitors are described in particular in patent or applications mentioned in Norman (Expert Opin. Ther. Patents (2012) 22(10):1233-1249).

Oclacitinib (N-Methyl{trans-4-[methyl(7H-pyrrolo[2,3-d]pyrimidin-4-yl)amino] cyclohexyl}methanesulfonamide) is of particular interest.

Upadacitinib ((3S,4R)-3-Ethyl-4-(3H-imidazo[1,2-a]pyr-rolo[2,3-e]pyrazin-8-yl)-N-(2,2,2-trifluoroethyl)pyrroli-dine-1-carboxamide) is also of interest. It is described in WO2009152133.

Filgotinib (N-[5-[4-[(1,1-Dioxo-1,4-thiazinan-4-yl) methyl]phenyl]-[1,2,4]triazolo [1,5-a]pyridin-2-yl]cyclo-propanecarboxamide) is also of interest.

One can also cite Abrocitinib (N-(cis-3-(Methyl(7H-pyr-rolo(2,3-d)pyrimidin-4-yl)amino)cyclobutyl)propane-1-sulfonamide).

In an embodiment, the JAK inhibitor is a JAK1/JAK2 inhibitor.

Ruxolitinib ((3R)-3-Cyclopentyl-3-[4-(7H-pyrrolo[2,3-d] pyrimidin-4-yl)pyrazol-1-yl]propanenitrile) is a janus kinase inhibitor (JAK inhibitor) with selectivity for subtypes JAK1 and JAK2. It was described in WO2007070514.

One can also cite Baricitinib (2-[1-Ethylsulfonyl-3-[4-(7H-pyrrolo[2,3-d]pyrimidin-4-yl)pyrazol-1-yl]azetidin-3-yl]acetonitrile)

Momelotinib (N-(cyanomethyl)-4-{2-[4-(morpholin-4-yl)anilino]pyrimidin-4-yl}benzamide) is also of interest.

Other inhibitors of enzymes of the JAK family are also described in WO2011113802, WO2012035039, WO2012066061, WO2013041539, WO2011130146, WO2013055645, WO2012160464, WO2014000032, WO2010142752 and WO2012160464 and in Kettle et al (Expert Opinion on Therapeutic Patents, 27:2, 127-143; Expert Opinion on Therapeutic Patents, 27:2, 145-161).

One can also cite Cerdulatinib (4-(Cyclopropylamino)-2-[4-(4-ethylsulfonylpiperazin-1-yl)anilino]pyrimidine-5-car-boxamide) which is an inhibitor of TYK2, JAK1, JAK2, JAK3, FMS, and SYK.

The JAK inhibitor can therefore be used in a method for treating, or in a method for preventing, occurrence of an adverse event induced by a treatment with an immune checkpoint inhibitor, comprising the step of administering an effective amount of the JAK inhibitor to a patient in need thereof. An effective amount, or therapeutic amount, is the amount sufficient to obtain beneficial or desired results, such as clinical results (remission of the symptoms of the immune related adverse events). The "effective amount" may depend upon the type of immune related adverse event, and upon the context in which it is being applied. In the context of the invention, an effective amount of a JAK inhibitor is, for example, an amount sufficient to achieve a reduction in the severity of the immune related adverse event, as compared to the response obtained without administration of the agonist.

As the immune related adverse event induced by the treatment with checkpoint inhibitors, one can cite, pneumo-nitis, hepatitis, hypophysitis, neurologic adverse effects (in-cluding encephalitis, myasthenia gravis, Guillain-Barre syn-drome), adrenal adverse effect, myositis, myocarditis, hematologic adverse effects (including hemolytic anemia, immune thrombocytopenic purpura, and aplastic anemia), nephritis, pancreatitis, and type 1 diabetes. All these diseases can be linked to the administration of ICI.

In particular, the adverse effect is a de novo effect, meaning that it was not present in the patient, or had not been diagnosed, prior to onset of the treatment of with the ICI.

Use of the JAK inhibitor is of particular interest for the treatment of a myotoxicity (in particular an immune-medi-ated myotoxicity), in particular fulminant myocarditis or fulminant diaphragmatic myositis (respiratory muscle myo-sitis involving the diaphragm). Fulminant myocarditis (FM) is a peculiar clinical condition (more frequently associated with anti-PD1/PL1 antibodies) and is an acute form of myocarditis, whose main characteristic is a rapidly progres-sive clinical course with the need for hemodynamic support, which has been shown to be linked to the presence of selective clonal T-cell populations, identical to those present in tumors and skeletal muscle, infiltrated in the myocardium, this event thus being a T-cell-driven drug reaction. This T-cell-driven mechanism is characteristic for immune-me-diated myotoxicity. In contrast, in immune-mediated colitis, the pathomechanisms are different since innate immune responses are also involved attested by the key role of gut microbiota and neutrophylic polynuclear leucocytes. In particular, ICI colitis can be treated with anti-TNF alfa (Som et al, World J Clin Cases. 2019 Feb. 26; 7(4): 405-418) whereas infliximab is considered not be used as first-line therapy after corticosteroids in patients with ICI-induced myocarditis (Cautela et al, Journal for ImmunoTherapy of Cancer 2020; 8:e001887).

This kind of fulminant myocarditis, when present in humans, doesn't mainly involve antibodies.

It is preferred when the JAK inhibitor is selected from the group consisting of ruxolitinib, tofacitinib, oclacitinib, baricitinib, peficitinib, fedratinib, upadacitinib, filgotinib, cerdulatinib, gandotinib, lestaurtinib, momelotinib, pacritinib and abrocitinib.

Ruxolitinib is of particular interest.

Tofacitinib is also of particular interest.

Baricitinib is also of particular interest.

The immune checkpoint inhibitor used for the patient's treatment before occurrence of the adverse effect is any such drug in this class.

In particular, one can cite:

PD-1 inhibitors: IgG4 PD1 antibody nivolumab, pembrolizumab, partalizumab (PDR001) developed by Novartis, pidilizumab developed by Cure Tech, AMP-224 or AMP-514 both developed by GlaxoSmithKline, cemiplimab developed by Regeneron and Sanofi, toripalimab developed by Shanghai Junshi, spartalizumab, developed by Novartis, cetrelimab (JNJ-63723283) developed by Janssen, or sasanlimab (PF-06801591) developed by Pfizer.

PD-L1 inhibitors: atezolizumab developed by Roche Genentech, avelumab developed by Merck Serono and Pfizer or durvalumab developed by AstraZeneca.

Anti-CTLA4: ipilimumab or tremelimumab.

The JAK inhibitor is used at a dosage similar to or up to 4 or even 10 times higher than those dosages preconized by the manufacturer and according to good practice in the art. Choice of the appropriate dosage may be adapted by the physician depending on the severity of the clinical presentation and evolution on treatment.

As a matter of illustration, the current dosing of ruxolitinib is comprised between 5 mg and 20 mg twice a day, depending on the disease, and of the platelets amount. Tofacitinib is also administered at these kind of amounts (from 5 mg to 20 mg twice a day).

It is thus preferred when the JAK inhibitor is administered via multiple administrations, in particular multiple daily administrations. As a matter of illustration, the JAK inhibitor can be administered twice daily to the patient.

As indicated above, the dose administered to the patient is chosen so as to be therapeutically effective. It is thus possible to use higher amount of such products for the first administration in order to try to quickly diminish the adverse effects, and then lower the dose when the clinical status of the patient improves.

It is generally envisaged to limit administration of the JAK inhibitor to the patient, and to stop the treatment when the patient general condition has improved. In a specific embodiment, the treatment should last for a few weeks or maximum months. For instance, a treatment may last from about three to twenty weeks, generally about four to ten weeks. In this case, there would be multiple administration of the JAK inhibitor provided to the patient.

The JAK inhibitor is generally in a form suitable for oral administration. However, it may be in a form suitable for injectable administration. Preferably, such administration is an intravenous injection, intra-muscular or subcutaneous injection.

In specific embodiment, the JAK inhibitor is in the form of a slow release composition, which would enable decreasing the number of administrations.

Even though the examples excluded the use of an immunosuppressant, in the context of the COVID-19 pandemic, it may be of interest to use an immunosuppressant together with the JAK inhibitor for treating the adverse effects.

In combination with administration of JAK inhibitors, as described above, glucocorticoids at high dose (up to 1 g/day methylprednisone equivalent for few days) and or other immunosuppressants may be also be used. These latter immunosuppressants are preferentially antimetabolites (such as mycofenolate mofetil, azathioprine, methotrexate), anti-calcineurin (also designated as calcineurin inhibitors) (ciclosporin, tacrolimus), mTOR inhibitors (sirolimus, temsirolimus, everolimus), anti-thymoglubin, intravenous immunoglobulin, interleukin-6 inhibitors (tocilizumab, siltuximab, sarilumab, sirukumab, olokizumab, clazakizumab), interleukin-1 pathway inhibitors (anakinra, rilonacept, canakinumab), TNF-α inhibitors, CTLA4 agonist or anti CD28. Other compounds that can be used also include basiliximab (chimeric mouse-human monoclonal antibody) or daclizumab (both binding to the a chain (CD25) of the IL-2 receptor of T cells), tocilizumab, also known as atlizumab, humanized monoclonal antibody against the interleukin-6 receptor (IL-6R), and alemtuzumab (monoclonal antibody that binds to CD52).

It is of particular interest to use corticoids. In another embodiment, it is of interest to use a CTLA4 agonist, in particular abatacept or belatacept. One can also use intravenous immunoglobulins (IVIg). One can use the JAK inhibitor in combination with both corticoids and the CTLA4 agonist, in particular abatacept.

It is also possible to use plasmapheresis to clear immune checkpoint inhibitor drug levels in the circulation. In this case, the scheme of administration of the JAK inhibitor (in particular Ruxolitinib or Tofacitinib) needs to be adapted.

The invention also relates to the JAK inhibitor for use as indicated above, it is administered with another immunosuppressant, or any other drug as disclosed below, including glucocorticoids, antimetabolites (such as mycophenolate mofetil, azathiatrine, methotrexate), calcineurin inhibitors (ciclosporin, tacrolimus), mtor inhibitors (sirolimus, temsirolimus, everolimus), anti-thymoglubin, intravenous immunoglobulin, interleukin-6 inhibitors (tocilizumab, siltuximab), anti CD52 (alemtuzumab), anti CD25 (basiliximab, daclizumab), interleukin-1 pathway inhibitors (anakinra, rilonacept, canakinumab), TNF-α inhibitors, IVIg and anti CD28. Said co-administration can be simultaneous, separate or sequential (spread out over time).

The invention also relates to a composition containing a JAK inhibitor and an immunosuppressant or any other drug as disclosed above, for simultaneous, separate or sequential (spread out over time) use thereof in the treatment or prevention of an adverse event induced by a treatment with an immune checkpoint inhibitor.

The invention also relates to a method for treating or preventing an adverse event induced by a treatment with an immune checkpoint inhibitor, comprising administering a therapeutically active amount of a JAK inhibitor to a subject in need thereof, with a simultaneous, separate or sequential (spread out over time) administration of an effective amount of an immunosuppressant to the subject.

The invention also relates to a JAK inhibitor for use thereof in the treatment of an adverse event induced by a treatment with an immune checkpoint inhibitor, in a patient in need thereof, wherein said patient has been subject to a plasmapheresis prior to administration of the JAK inhibitor. As indicated above, such plasmapheresis makes it possible to clear immune check-point inhibitors levels in the circulation of the patient.

The invention also relates to a method for treating a subject in need thereof, wherein said subject present an adverse effect induced by a treatment with an immune checkpoint inhibitor, comprising performing a plasmapheresis to the subject (so as to clear immune checkpoint inhibitors levels in the circulation of the subject) and administering an effective amount of a JAK inhibitor (alone or with another immunosuppressant) prior and after plasmapheresis.

The invention also relates to use of a JAK inhibitor as disclosed above, for the preparation of a medicament intended to treat or prevent an adverse event induced by a treatment with an immune checkpoint inhibitor in a patient. This medicament can also be a combination comprising an immunosuppressant as disclosed above.

The invention makes it possible to prevent the occurrence or recurrence of severe immune-related adverse events related to Immune Checkpoint Inhibitors (ICI-irAE). Indeed, the results of transcriptomics analysis reported herein show that ICIinduced myositis differs from spontaneous inflammatory myopathies in terms of gene expressions. It is thus envisaged to combine the administration of a JAK inhibitor and an ICI.

The invention thus relates to a composition containing a JAK inhibitor and an immune checkpoint inhibitor, for simultaneous, separate or sequential (spread out over time) use thereof in the treatment of cancer.

The invention also relates to a method for treating a cancer in a subject, comprising administering a therapeutically active amount of a JAK inhibitor to a subject in need thereof, with a simultaneous, separate or sequential (spread out over time) administration of an effective amount of an immune checkpoint inhibitor to the subject.

The cancer is, in particular, selected from the group consisting of bladder carcinoma, breast carcinoma, cervical carcinoma, cholangiocarcinoma, colorectal carcinoma, gastric sarcoma, glioma, lung carcinoma, lymphoma, acute and chronic lymphoid and myeloid leukemias, melanoma, multiple myeloma, osteosarcoma, ovarian carcinoma, pancreatic carcinoma, prostate carcinoma, stomach carcinoma, kidney carcinoma, a head and neck tumor, and a solid tumor.

In particular, it is possible to associate nivolumab and ruxolitinib, notably for treating pulmonary adenocarcinoma (even when metastatic).

As shown in The FIGURE, STAT1, IFI6, TAP1, IRF1, FCγR3A genes were largely upregulated, whereas STAT2, STAT3 and STAT6 genes were also upregulated but at a lower level.

It is thus envisaged to use an inhibitor of these genes (DNA or RNA) or of the proteins in the same ways as the JAK inhibitor. Indeed, it can be advantageous to use an inhibitor for a gene, an RNA or protein that is located downstream JAK, so as to be more specific and potentially reduce adverse effects that could be associated with a JAK inhibitor administration.

The invention thus relates to an inhibitor of STAT1 for use thereof for the treatment of immune-related adverse events induced by a treatment with an immune checkpoint inhibitor.

The invention thus relates to a composition containing an inhibitor of STAT1 and an immune checkpoint inhibitor, for simultaneous, separate or sequential (spread out over time) use thereof in the treatment of cancer.

The invention thus relates to a composition containing an inhibitor of STAT1 and an immunosuppressant, for simultaneous, separate or sequential (spread out over time) use thereof in the treatment or prevention of an adverse event induced by a treatment with an immune checkpoint inhibitor.

The invention also relates to a method for treating or preventing an adverse event induced by a treatment with an immune checkpoint inhibitor, comprising administering a therapeutically active amount of an inhibitor of STAT1 to a subject in need thereof, with a simultaneous, separate or sequential (spread out over time) administration of an effective amount of an immunosuppressant to the subject.

The invention also relates to an inhibitor of STAT1 for use thereof in the treatment of an adverse event induced by a treatment with an immune checkpoint inhibitor, in a patient in need thereof, wherein said patient has been subject to a plasmapheresis prior to administration of the STAT1 inhibitor.

The invention also relates to a method for treating a subject in need thereof, wherein said subject present an adverse effect induced by a treatment with an immune checkpoint inhibitor, comprising performing a plasmapheresis to the subject (so as to clear immune checkpoint inhibitors levels in the circulation of the subject) and administering an effective amount of an inhibitor of STAT1 (alone or with another immunosuppressant) prior and after plasmapheresis.

The invention also relates to use of an inhibitor of STAT1 as disclosed above, for the preparation of a medicament intended to treat or prevent an adverse event induced by a treatment with an immune checkpoint inhibitor in a patient. This medicament can also be a combination comprising an immunosuppressant as disclosed above.

The invention thus relates to a composition containing an inhibitor of STAT1 and an immune checkpoint inhibitor, for simultaneous, separate or sequential (spread out over time) use thereof in the treatment of cancer.

The invention also relates to a method for treating a cancer in a subject, comprising administering a therapeutically active amount of an inhibitor of STAT1 to a subject in need thereof, with a simultaneous, separate or sequential (spread out over time) administration of an effective amount of an immune checkpoint inhibitor to the subject.

As an inhibitor of STAT1, one can cite, as an illustration, fludarabine (CAS Number 21679-14-1), which is a STAT1 activation inhibitor (it down-regulates STAT1 by inhibiting STAT1 phosphorylation in both normal and cancer cells) but not of other STATs. It is used to treat various hematological malignancies, such as chronic lymphocytic leukemia.

One can also cite Nifuroxazide (CAS 965-52-6, an oral nitrofuran antibiotic commonly used as an anti-diarrheal agent).

One can also use PIAS (protein inhibitor of activated STAT) proteins (Liu et al Proc Natl Acad Sci USA, 1998 Sep. 1; 95(18):10626-31).

The invention thus relates to an inhibitor of IFI6 (Interferon alpha-inducible protein 6) for use thereof for the treatment of immune-related adverse events induced by a treatment with an immune checkpoint inhibitor.

The invention thus relates to a composition containing an inhibitor of IFI6 and an immune checkpoint inhibitor, for simultaneous, separate or sequential (spread out over time) use thereof in the treatment of cancer.

The invention thus relates to a composition containing an inhibitor of IFI6 and an immunosuppressant, for simultaneous, separate or sequential (spread out over time) use thereof in the treatment or prevention of an adverse event induced by a treatment with an immune checkpoint inhibitor.

The invention also relates to a method for treating or preventing an adverse event induced by a treatment with an immune checkpoint inhibitor, comprising administering a therapeutically active amount of an inhibitor of IFI6 to a subject in need thereof, with a simultaneous, separate or sequential (spread out over time) administration of an effective amount of an immunosuppressant to the subject.

The invention also relates to an inhibitor of IFI6 for use thereof in the treatment of an adverse event induced by a treatment with an immune checkpoint inhibitor, in a patient in need thereof, wherein said patient has been subject to a plasmapheresis prior to administration of the IFI6 inhibitor.

The invention also relates to a method for treating a subject in need thereof, wherein said subject present an adverse effect induced by a treatment with an immune checkpoint inhibitor, comprising performing a plasmapheresis to the subject (so as to clear immune checkpoint inhibitors levels in the circulation of the subject) and administering an effective amount of an inhibitor of IFI6 (alone or with another immunosuppressant) prior and after plasmapheresis.

The invention also relates to use of an inhibitor of IFI6 as disclosed above, for the preparation of a medicament intended to treat or prevent an adverse event induced by a treatment with an immune checkpoint inhibitor in a patient. This medicament can also be a combination comprising an immunosuppressant as disclosed above.

The invention thus relates to a composition containing an inhibitor of IFI6 and an immune checkpoint inhibitor, for simultaneous, separate or sequential (spread out over time) use thereof in the treatment of cancer.

The invention also relates to a method for treating a cancer in a subject, comprising administering a therapeutically active amount of an inhibitor of IFI6 to a subject in need thereof, with a simultaneous, separate or sequential (spread out over time) administration of an effective amount of an immune checkpoint inhibitor to the subject.

As an inhibitor of IFI6, one can use an antibody against this protein, as the ones developed and sold by various companies (Sigma Aldrich, Thermofisher).

The invention thus relates to a TAP1 (Transporter associated with antigen processing 1) inhibitor for use thereof for the treatment of immune-related adverse events induced by a treatment with an immune checkpoint inhibitor.

The invention thus relates to a composition containing an inhibitor of TAP1 and an immune checkpoint inhibitor, for simultaneous, separate or sequential (spread out over time) use thereof in the treatment of cancer.

The invention thus relates to a composition containing an inhibitor of TAP1 and an immunosuppressant, for simultaneous, separate or sequential (spread out over time) use thereof in the treatment or prevention of an adverse event induced by a treatment with an immune checkpoint inhibitor.

The invention also relates to a method for treating or preventing an adverse event induced by a treatment with an immune checkpoint inhibitor, comprising administering a therapeutically active amount of an inhibitor of TAP1 to a subject in need thereof, with a simultaneous, separate or sequential (spread out over time) administration of an effective amount of an immunosuppressant to the subject.

The invention also relates to an inhibitor of TAP1 for use thereof in the treatment of an adverse event induced by a treatment with an immune checkpoint inhibitor, in a patient in need thereof, wherein said patient has been subject to a plasmapheresis prior to administration of the TAP1 inhibitor.

The invention also relates to a method for treating a subject in need thereof, wherein said subject present an adverse effect induced by a treatment with an immune checkpoint inhibitor, comprising performing a plasmapheresis to the subject (so as to clear immune checkpoint inhibitors levels in the circulation of the subject) and administering an effective amount of an inhibitor of TAP1 (alone or with another immunosuppressant) prior and after plasmapheresis.

The invention also relates to use of an inhibitor of TAP1 as disclosed above, for the preparation of a medicament intended to treat or prevent an adverse event induced by a treatment with an immune checkpoint inhibitor in a patient. This medicament can also be a combination comprising an immunosuppressant as disclosed above.

The invention thus relates to a composition containing an inhibitor of TAP1 and an immune checkpoint inhibitor, for simultaneous, separate or sequential (spread out over time) use thereof in the treatment of cancer.

The invention also relates to a method for treating a cancer in a subject, comprising administering a therapeutically active amount of an inhibitor of TAP1 to a subject in need thereof, with a simultaneous, separate or sequential (spread out over time) administration of an effective amount of an immune checkpoint inhibitor to the subject.

As TAP1 inhibitor, one can cite the viral TAP inhibitor ICP47 (Matschulla et al Sci Rep 7, 2933 (2017)).

The invention thus relates to an inhibitor of IRF1 (Interferon regulatory factor 1) for use thereof for the treatment of immune-related adverse events induced by a treatment with an immune checkpoint inhibitor.

The invention thus relates to a composition containing an inhibitor of IRF1 and an immune checkpoint inhibitor, for simultaneous, separate or sequential (spread out over time) use thereof in the treatment of cancer.

The invention thus relates to a composition containing an inhibitor of IRF1 and an immunosuppressant, for simultaneous, separate or sequential (spread out over time) use thereof in the treatment or prevention of an adverse event induced by a treatment with an immune checkpoint inhibitor.

The invention also relates to a method for treating or preventing an adverse event induced by a treatment with an immune checkpoint inhibitor, comprising administering a therapeutically active amount of an inhibitor of IRF1 to a subject in need thereof, with a simultaneous, separate or sequential (spread out over time) administration of an effective amount of an immunosuppressant to the subject.

The invention also relates to an inhibitor of IRF1 for use thereof in the treatment of an adverse event induced by a treatment with an immune checkpoint inhibitor, in a patient in need thereof, wherein said patient has been subject to a plasmapheresis prior to administration of the IRF1 inhibitor.

The invention also relates to a method for treating a subject in need thereof, wherein said subject present an adverse effect induced by a treatment with an immune checkpoint inhibitor, comprising performing a plasmapheresis to the subject (so as to clear immune checkpoint inhibitors levels in the circulation of the subject) and administering an effective amount of an inhibitor of IRF1 (alone or with another immunosuppressant) prior and after plasmapheresis.

The invention also relates to use of an inhibitor of IRF1 as disclosed above, for the preparation of a medicament intended to treat or prevent an adverse event induced by a treatment with an immune checkpoint inhibitor in a patient.

This medicament can also be a combination comprising an immunosuppressant as disclosed above.

The invention thus relates to a composition containing an inhibitor of IRF1 and an immune checkpoint inhibitor, for simultaneous, separate or sequential (spread out over time) use thereof in the treatment of cancer.

The invention also relates to a method for treating a cancer in a subject, comprising administering a therapeutically active amount of an inhibitor of IRF1 to a subject in need thereof, with a simultaneous, separate or sequential (spread out over time) administration of an effective amount of an immune checkpoint inhibitor to the subject.

As IRF1 inhibitory strategies, one can use the ones listed in Szelag et al (Oncotarget. 2016 Jul. 26; 7(30): 48788-48812), for instance using siRNAs, minocycline (Nikodemova et al, J Biol Chem. 2007 May 18; 282(20): 15208-16), or HS-Cf (Liu et al, J Clin Immunol. 2011 December; 31(6):1131-42), or in Antoczyk (Front. Immunol., 24 May 2019|https://doi.org/10.3389/fimmu.2019.01176).

The invention thus relates to a FCγR3A (Fc gamma receptor 3 A) inhibitor for use thereof for the treatment of immune-related adverse events induced by a treatment with an immune checkpoint inhibitor.

The invention thus relates to a composition containing a FCγR3A inhibitor and an immune checkpoint inhibitor, for simultaneous, separate or sequential (spread out over time) use thereof in the treatment of cancer.

The invention thus relates to a composition containing a FCγR3A inhibitor and an immunosuppressant, for simultaneous, separate or sequential (spread out over time) use thereof in the treatment or prevention of an adverse event induced by a treatment with an immune checkpoint inhibitor.

The invention also relates to a method for treating or preventing an adverse event induced by a treatment with an immune checkpoint inhibitor, comprising administering a therapeutically active amount of a FCγR3A inhibitor to a subject in need thereof, with a simultaneous, separate or sequential (spread out over time) administration of an effective amount of an immunosuppressant to the subject.

The invention also relates to a FCγR3A inhibitor for use thereof in the treatment of an adverse event induced by a treatment with an immune checkpoint inhibitor, in a patient in need thereof, wherein said patient has been subject to a plasmapheresis prior to administration of the FCγR3A inhibitor.

The invention also relates to a method for treating a subject in need thereof, wherein said subject present an adverse effect induced by a treatment with an immune checkpoint inhibitor, comprising performing a plasmapheresis to the subject (so as to clear immune checkpoint inhibitors levels in the circulation of the subject) and administering an effective amount of a FCγR3A inhibitor (alone or with another immunosuppressant) prior and after plasmapheresis.

The invention also relates to use of a FCγR3A inhibitor as disclosed above, for the preparation of a medicament intended to treat or prevent an adverse event induced by a treatment with an immune checkpoint inhibitor in a patient. This medicament can also be a combination comprising an immunosuppressant as disclosed above.

The invention thus relates to a composition containing a FCγR3A inhibitor and an immune checkpoint inhibitor, for simultaneous, separate or sequential (spread out over time) use thereof in the treatment of cancer.

The invention also relates to a method for treating a cancer in a subject, comprising administering a therapeutically active amount of a FCγR3A inhibitor to a subject in need thereof, with a simultaneous, separate or sequential (spread out over time) administration of an effective amount of an immune checkpoint inhibitor to the subject.

The invention thus relates to an inhibitor of STAT2, STAT3 or STAT6 for use thereof for the treatment of immune-related adverse events induced by a treatment with an immune checkpoint inhibitor.

The invention thus relates to a composition containing an inhibitor of STAT2, STAT3 or STAT6 and an immune checkpoint inhibitor, for simultaneous, separate or sequential (spread out over time) use thereof in the treatment of cancer.

The invention thus relates to a composition containing an inhibitor of STAT2, STAT3 or STAT6 and an immunosuppressant, for simultaneous, separate or sequential (spread out over time) use thereof in the treatment or prevention of an adverse event induced by a treatment with an immune checkpoint inhibitor.

The invention also relates to a method for treating or preventing an adverse event induced by a treatment with an immune checkpoint inhibitor, comprising administering a therapeutically active amount of an inhibitor of STAT2, STAT3 or STAT6 to a subject in need thereof, with a simultaneous, separate or sequential (spread out over time) administration of an effective amount of an immunosuppressant to the subject.

The invention also relates to an inhibitor of STAT2, STAT3 or STAT6 for use thereof in the treatment of an adverse event induced by a treatment with an immune checkpoint inhibitor, in a patient in need thereof, wherein said patient has been subject to a plasmapheresis prior to administration of the IRF1 inhibitor.

The invention also relates to a method for treating a subject in need thereof, wherein said subject present an adverse effect induced by a treatment with an immune checkpoint inhibitor, comprising performing a plasmapheresis to the subject (so as to clear immune checkpoint inhibitors levels in the circulation of the subject) and administering an effective amount of an inhibitor of STAT2, STAT3 or STAT6 (alone or with another immunosuppressant) prior and after plasmapheresis.

The invention also relates to use of an inhibitor of STAT2, STAT3 or STAT6 as disclosed above, for the preparation of a medicament intended to treat or prevent an adverse event induced by a treatment with an immune checkpoint inhibitor in a patient. This medicament can also be a combination comprising an immunosuppressant as disclosed above.

The invention thus relates to a composition containing an inhibitor of STAT2, STAT3 or STAT6 and an immune checkpoint inhibitor, for simultaneous, separate or sequential (spread out over time) use thereof in the treatment of cancer.

The invention also relates to a method for treating a cancer in a subject, comprising administering a therapeutically active amount of an inhibitor of STAT2, STAT3 or STAT6 to a subject in need thereof, with a simultaneous, separate or sequential (spread out over time) administration of an effective amount of an immune checkpoint inhibitor to the subject.

DESCRIPTION OF THE FIGURES

The FIGURE: Spatial transcriptomic analysis was performed on skeletal muscle biopsies from ICI-patients with myositis (n=5) and histological normal muscle tissues (n=5; from ICI-patients without myositis or non-ICI-patients).

Unsupervised cluster analysis identified 13 clusters including two (cluster 1 and 12) corresponding to aeras with inflammatory infiltrates. Up-regulation of JAK1/2-STAT1 stimulated genes are represented in inflammatory clusters (1 and 12) and in two representative clusters (0 and 2) without inflammatory infiltrates

EXAMPLES

Example 1

A 67-year-old man was treated for metastatic pulmonary adenocarcinoma with nivolumab as second-line therapy but developed myalgia, diplopia and bilateral ptosis after 2 treatments with nivolumab (4 weeks after treatment initiation).

Myositis was suspected due to increased creatine kinase levels and confirmed by muscle biopsy. Myocarditis was confirmed with troponin increase, premature ventricular contractions and deterioration of left-ventricular ejection fraction with no signs of acute coronary syndrome on angiogram.

The patient was treated with glucocorticoids and one exchange of plasmapheresis. However, due to positive SARS-Cov-2 infection, detected during hospitalization, and the uncertainty of glucocorticoids use for COVID-19 at that time, corticosteroids were tapered.

Ruxolitinib was initiated (15 mg twice daily), with prompt decrease in troponin and improvement of oculomotor disorders. Ruxolitinib was continued for 1 month at 15 mg twice daily, with complete resolution of myotoxicity; there was no evidence of tumor progression at 3 months.

Immune-checkpoint inhibitors (ICI)-associated myotoxicities (myocarditis and myositis) are infrequent but potentially fatal immune-related adverse events (irAE). Pathologically, ICI-myotoxicities are characterized by muscle infiltration of macrophages and T lymphocytes; the mechanism of muscle death is partly due proinflammatory cytokine production such as interferons.

Ruxolitinib, an oral selective inhibitor of JAK1 and JAK2 resulted in symptomatic relief of myotoxicity with no effect on tumor progression in follow-up.

This illustrates a role for JAK-inhibitors in the treatment of severe ICI-irAE.

Ten additional patients were treated. It is reminded here that the myotoxicity related to ICI exposure has the highest fatality among all type of immune related adverse event irAE. The only therapy currently recommended by experts are corticosteroids on the front line, but patients are frequently refractory to corticosteroids. Finally, it is recalled that a positive effect of abatacept was shown in patients with myotoxicity (WO 2020/161045). In order to decrease life-threatening major cardiovascular and myotoxic events for these patients with and ICI-myotoxicity, JAK inhibitors were used in combination with corticosteroids and abatacept. JAK inhibitors were also used to decrease corticosteroids dose since these latter are associated with (i) a decrease ICI efficacy and (ii) an increased risk of infectious and metabolic complications.

Patients:

Eleven ICI patients with irAE were treated. Patients were 69,9±13.2 years and mainly male (73%). Four patients had adenocarcinoma (colon: n=1; lung; n=2 and uterus: n=1), three patients had epidermoid carcinoma (skin: n=1; oropharynx n=1; unknown primitive n=1), two had urothelial or kidney carcinoma, one had thymoma, and one had melanoma.

Patients were treated with anti-PD1/PDL-1 therapy (PD1, n=10; PDL1: n=1). The mean time to onset from ICI exposure to irAE was 47.9±44.1 days and all patients were diagnosed as myocarditis and/or myositis involving respiratory and peripheral muscles. Six had concomitant irAE including 5 myasthenia like symptoms, 1 hepatitis, 1 thyroiditis.

All patients received ≥1 mg/kg/d prednisone. All but one patient (the 67 year old patient disclosed above) received JAK inhibitors in combination with abatacept. The first patient did not receive abatacept since he was also positive for SARS-CoV2 but evolved favorably as disclosed above. The doses of abatacept and the number of injections were based on the bodyweight and the clinical response.

Treatment:

Ruxolinitinib (JAK1/2 inhibitors) was used as JAK inhibitors. Ruxolitinib posology was 10 to 30 mg/d depending on the hemoglobin level and evolution curse of the ICI-myotoxicity. The treatment duration of JAK inhibitors ranged from 12 to 31 days based on patient outcome and hematological tolerance.

Patients Out-Come:

During the first 3 months follow-up among the 11 patients no death related to an irAE was recorded (three deaths were recorded, that were not related to irAE (hemorrhagic choc n=1; COVID19 n=2). All concurrent irAE evolved favorably.

Example 2

RNA-sequencing of muscle tissue was performed to identify the pathological mechanisms involved in ICI-induced myositis compared to normal tissue or other idiopathic inflammatory myopathies (paraneoplastic dermatomyositis, immune-mediated necrotizing myopathy, inclusion body myositis). A total of 30 samples (5 groups of 6 patients) were studied using unsupervised analysis, differentially expressed gene analysis, and pathways analysis.

ICI-induced myositis clustered in a unique subgroup different from both controls and patients with other type of myositis. These results demonstrate that ICI-induced myositis pathomechanisms (genes expression) are specific.

ICI-induced myositis represented a specific cluster with more than 6 000 genes differentially expressed compared to healthy controls. A gene set enrichment analysis was performed on the up and down-regulated genes. In the top 10 identified pathways, the interferon gamma-mediated signaling pathways and the type I interferon signaling pathways were found, showing the importance of JAK-STAT pathway.

In more details, although irAE show limited clinical similarities to their spontaneous auto-immune counterparts, ICI induce unique pathomechanisms. Bulk transcriptomic analysis of muscle tissues from patients with spontaneous myositis (DM: Dermatomyositis; IBM inclusion body myositis; IMNM: immune mediated necrotizing myopathies and HD healthy donors) and ICI-induced myositis was performed.

Unsupervised cluster analysis demonstrated that irAE represent a unique cluster different from spontaneous auto-immune diseases involving CD8+ T-cells (hierarchical analysis), showing that conventional therapeutic approaches cannot necessarily be applied to irAE. Hence, irAE are a unique condition different from their spontaneous auto-immune counterparts.

To decipher the specific pathomechanisms of irAE, peripheral mononuclear blood cells FACS analysis in patients with ICI-myositis (n=10) and ICI-controls (n=10) was first performed.

ICI-myositis showed a reduced proportion of CD8+ T-cells which harbored an activated phenotype suggesting a muscular homing. Indeed, muscular spatial transcriptomic analysis of ICI-myositis (n=5) showed a CD8+ T-cells enrichment vs. muscles of controls (n=5; normal histological muscle) (10×Genomics®). Cells deconvolution analysis (xCell signature analysis in inflammatory clusters) demonstrated that CD8+ T-cells exhibited an activated phenotype with a cytotoxic activity (granzyme and perforin).

Immune pathways analysis (IPA, Ingenuty®) confirms the activation interferon (IFN)-γ signaling with the up-regulation of JAK1/2-STAT1 stimulated genes. In particular, STAT1, IFI6, TAP1, IRF1, FCγR3A were largely upregulated in areas with muscle inflammation in ICI patients compared to aeras without inflammation (ICI-patients and controls), whereas STAT2, STAT3 and STAT6 were also upregulated although a bit less (The FIGURE). Hence, the genes downstream the JAK1/2 pathway are upregulated in the inflammatory clusters and not in the no inflammatory clusters (0 and 2).

One can note that JAK is mildly up-regulated, which is believed to be due to the fact that JAK is only activated once it is phosphorylated.

Hence, irAE are CD8+ T cell driven condition involving JAK/STAT signaling.

In addition to CD8+ T cells, a high density of monocytes/macrophages within the muscles of ICI-myositis patients was found. Spatial transcriptomic analysis showed that the macrophages displayed a pro-inflammatory phenotype (phagocytosis and pro-inflammatory cytokines production: M1-polarization) in response to Th1 lymphocytes producing IFN-γ.

IFNγ-JAK-STAT pathway plays a critical role in the production of CXCL-9 and CXCL-10 chemokines, that were found highly up-regulated in ICI-myositis (in inflammatory clusters). CXCL-9/10 is crucial for the recruitment of CD8+ T-cells. Together, the data showed the presence of cytotoxic CD8+ T-cells within the muscles and a strong activation of the IFNγ-JAK-STAT pathway. Muscle damages and the IFNγ-Th1 environment drive the M1 polarization of the macrophages. The IFNγ-JAK-STAT activation in M1 macrophages leads to CD8+ T-cells recruitment via CXCL9/10 chemokines.

The invention claimed is:

1. A method for treating or preventing an immune-related adverse event, wherein the immune-related adverse event is induced by treatment with an immune checkpoint inhibitor, the method comprising administering a therapeutically effective amount of ruxolitinib to a subject in need thereof;

wherein the adverse event is not toxidermia, colitis, or arthritis.

2. The method of claim 1, wherein the immune-related adverse event is an immune-mediated disease selected from myocarditis, pneumonitis, hepatitis, hypophysitis, neurologic adverse effect, adrenal adverse effect, myositis, hematologic adverse effect, pancreatitis, endocrinological adverse effect, nephritis, or a combination thereof.

3. The method of claim 1, wherein the immune-related adverse event is a de novo event, not related to a preexisting immune condition of the subject before treatment with the immune checkpoint inhibitor.

4. The method of claim 1, wherein the immune-related adverse event is an immune-mediated myotoxicity.

5. The method of claim 4, wherein the immune-mediated myotoxicity is fulminant myocarditis or fulminant respiratory muscle myositis involving the subject's diaphragm.

6. The method of claim 1, wherein the immune checkpoint inhibitor is selected from PD-1 inhibitors, PD-L1 inhibitors, anti-CTLA4, or a combination thereof.

7. The method of claim 1, wherein the immune checkpoint inhibitor is a PD-1 inhibitor selected from nivolumab, pembrolizumab, pidilizumab, AMP-224, AMP-514, cemiplimab, toripalimab, spartalizumab, cetrelimab, sasanlimab, or a combination thereof.

8. The method of claim 1, wherein the immune checkpoint inhibitor is a PD-L1 inhibitor selected from atezolizumab, avelumab, durvalumab, or a combination thereof.

9. The method of claim 1, wherein the immune checkpoint inhibitor is an anti-CTLA4 selected from ipilimumab, tremelimumab, or a combination thereof.

10. The method of claim 1 comprising multiple administrations of the ruxolitinib to the subject.

11. The method of claim 1, wherein the ruxolitinib is administered to the subject over a period of three weeks to twenty-four weeks.

12. The method of claim 1, wherein the ruxolitinib is administered to the subject in a slow-release composition.

13. The method of claim 1, further comprising administering a therapeutically effective amount of an immunosuppressant with the ruxolitinib.

14. The method of claim 13, wherein the immunosuppressant is a glucocorticoid, a CTLA4 agonist, or a combination thereof.

15. A method for treating cancer in a subject in need thereof comprising administering to the subject a therapeutically effective amount of ruxolitinib and a therapeutically effective amount of an immune checkpoint inhibitor, wherein the method prevents occurrence or recurrence of a severe immune-related adverse event related to use of the immune checkpoint inhibitor in the treatment of cancer.

16. The method of claim 15, further comprising administering to the subject a therapeutically effective amount of an immunosuppressant.

17. The method of claim 15, wherein the ruxolitinib and the immune checkpoint inhibitor are administered separately or sequentially.

18. The method of claim 15, wherein the immune checkpoint inhibitor is selected from nivolumab, pembrolizumab, pidilizumab, AMP-224, AMP-514, cemiplimab, toripalimab, spartalizumab, cetrelimab, sasanlimab, atezolizumab, avelumab, durvalumab, ipilimumab, tremelimumab, or a combination thereof.

19. The method of claim 13, wherein the immunosuppressant is abatacept.

20. The method of claim 16, wherein the immunosuppressant is abatacept.

21. A method of treating or preventing an immune-related adverse event induced by a treatment with an immune checkpoint inhibitor in a subject comprising administering to the subject ruxolitinib, abatacept, and a corticosteroid, wherein the administering is simultaneous, separate, or sequential.

* * * * *